US007175993B2

(12) United States Patent
Salamone et al.

(10) Patent No.: US 7,175,993 B2
(45) Date of Patent: Feb. 13, 2007

(54) TAXOL IMMUNOASSAY

(75) Inventors: Salvatore J. Salamone, Stockton, NJ (US); Jodi Blake Courtney, Doylestown, PA (US); Dennis Stocker, Yardley, PA (US); Mahmoud Ahmed ElSohly, Oxford, MS (US); Waseem Gul, Oxford, MS (US)

(73) Assignee: Saladax Biomedical, Inc., Bethlehem, PA (US)

( * ) Notice: Subject to any disclaimer, the term of this patent is extended or adjusted under 35 U.S.C. 154(b) by 0 days.

(21) Appl. No.: 11/301,101

(22) Filed: Dec. 12, 2005

(65) Prior Publication Data

US 2006/0099665 A1    May 11, 2006

Related U.S. Application Data

(63) Continuation of application No. 11/191,497, filed on Jul. 28, 2005, now abandoned, which is a continuation-in-part of application No. 11/044,667, filed on Jan. 27, 2005, now abandoned.

(60) Provisional application No. 60/592,017, filed on Jul. 29, 2004.

(51) Int. Cl.
*G01N 33/53* (2006.01)
*G01N 33/532* (2006.01)
*G01N 33/551* (2006.01)
*C07K 16/00* (2006.01)
*C07K 1/13* (2006.01)
*C07K 1/04* (2006.01)
*C07D 305/14* (2006.01)

(52) U.S. Cl. ............... 435/7.93; 435/7.1; 436/523; 436/524; 436/544; 436/548; 436/815; 530/388.9; 530/389.8; 530/402; 530/403; 549/510

(58) Field of Classification Search ............... 435/7.1, 435/7.93; 549/510; 530/388.9, 389.8, 402, 530/403; 436/544, 548, 815, 523, 524
See application file for complete search history.

(56) References Cited

U.S. PATENT DOCUMENTS

| 3,996,334 | A | 12/1976 | Hartman et al. |
|---|---|---|---|
| 4,016,146 | A | 4/1977 | Soares |
| 4,039,385 | A | 8/1977 | Ullman et al. |
| 4,269,511 | A | 5/1981 | Erwin |
| 4,420,568 | A | 12/1983 | Wang et al. |
| 5,101,015 | A | 3/1992 | Brynes et al. |
| 5,501,987 | A | 3/1996 | Ordonez et al. |
| 5,756,301 | A | * 5/1998 | Erlanger et al. ......... 435/7.23 |

OTHER PUBLICATIONS

Leu et al., Characterization of polyclonal and monoclonal anti-taxol antibodies and measurement of taxol in serum., 1993, Cancer Research, vol. 53, pp. 1388-1391.*

Grothaus et al., Taxane-specific monoclonal antibodies: measurement of taxol, baccatin III, and "total taxanes" in Taxus brevifolia extracts by enzyme immunoassay. Journal of natuaral products, 1995, vol. 58, No. 7, pp. 1003-1014.*

Grothaus et al., An enzyme immunoassay for the determination of taxol and taxanes in Taxus sp. tissues and hyman plasma, 1993, Journal of immunological methods, vol. 158, pp. 5-15.*

Holmes et al., Phase II Study of Taxol in Patients (PT) with Metastatic Breast Cancer (MBC), Proc. Am. Soc. Clin. Oncol., 10:60 (Mar. 10, 1991).

Einzig et al., Phase II Study of Taxol (T) in patients (Pts) with Advanced Ovarian Cancer, Proc. Am. Assoc. Cancer Res., 31 (1114):187 (Mar. 1990).

Gurney, Howard, Dose Calculation of Anticancer Drugs: A Review of the Current Practice and introduction of an Alternative, Journal of Clinical Oncology, 14(9):2590-2611 (Sep. 1996).

Hon et al., Making TDM work to optimize cancer chemotherapy: a multidisciplinary team approach, Clinical Chemistry, 44(2):388-400 (1998).

Huston et al., Protein engineering of antibody sites: Recovery of specific activity in an anti-digoxin single-chain Fv analogue produced in *Escherichia coli*, Proc. Natl. Acad. Sci. USA, 85:5879-5883 (Aug. 1998).

Bird et al., Synthesis of New d-Propoxyphene Derivatives and the Development of a Microparticle-Based Immunoassay for the Detection of Propoxyphene and Norpropoxyphene, Bioconjugate Chem., 8:385-390 (1997).

Li et al., New Synthesis and Characterization of (+)-Lysergic Acid Diethylamide (LSD) Derivatives and the Development of a Microparticle-Based Immunoassay for the Detection of LSD and its Metabolites, Bioconjugate Chem., 8:896-905 (1997).

Wu et al., Synthesis of New d-Propoxyphene Derivatives and the Development of a Microparticle-Based Immunoassay for the Detection of Propoxyphene and Norpropoxyphene, Bioconjugate Chem., 8:385-390 (1997).

Salamone et al., A Non-Cannabinoid Immunogen Used to Elicit Antibodies with Broad Cross-Reactivity to Cannabinoid Metabolites, J. Forensic Sciences, 821-826 (Jul. 1998).

(Continued)

*Primary Examiner*—Long V. Le
*Assistant Examiner*—Shafiqul Haq

(57) ABSTRACT

Novel conjugates of taxol and novel taxol immunogens derived from the 9 and 7 positions of taxol and monoclonal antibodies generated by these taxol linked immunogens are useful in immunoassays for the quantification and monitoring of taxol in biological fluids.

17 Claims, No Drawings

OTHER PUBLICATIONS

Coligan, J.E. et al., eds., Current Protocols in Immunology, 2.5.1-2.5.17, (1992), Wiley & Sons, NY.

Bicamumpaka, et al., Development of a fluorescence polarization immunoassay (FPIA) for the quantitative determination of paclitaxel, Journal of Immunological Methods, 212(1):1-7 (1998).

Bignami et al., Monoclonal antibodies to taxanes that neutralize the biologlcal activity of paclitaxel, Cancer Letters, 126:127-133 (1998).*

Grothaus, et al., Taxane-Specific Monoclonal Antibodies: Measurement of Taxol, Baccatin III and "Total Taxanes" in Taxus Brevifolia Extracts by Enzyme Immunoassay, Journal of Natural Products, 58(7):1003-14 (Jul. 1995).*

Grothaus et al., An enzyme immunoassay for the determination of taxol and taxanes in Taxus sp. tissues and human plasma, Journal of Immunological Methods, 158:5-15 (1993).*

Guillemard et al., Development of a Very Sensitive Luminescence Assay for the Measurement of Paclitaxel and Related Taxanes, Anticancer Research, 19:5127-30 (1999).*

Guillemard, et al., A radioimmunoassay for the measurement of paclitaxel and taxanes in biological specimens using commercially available reagents, Oncology Reports, 6:1257-59 (1999).*

Leu et al., Characterization of Polyclonal and Monoclonal Anti-Taxol Antibodies and Measurement of Taxol in Serum, Cancer Research, 53:1388-91 (Mar. 15, 1993).*

Morais et al., A tubulin-based fluorescent polarization assay for paclitaxel, Analytical Biochemistry, 321:44-9 (2003).*

O'Boyle et al., Development of Two Radioimmunoassays to Detect Paclitaxel in Sera and in Cerebrospinal, Ascitic and Pleural Fluids, Cancer, 79(5):1022-30 (1997).*

* cited by examiner

TAXOL IMMUNOASSAY

CROSS-REFERENCE TO RELATED APPLICATION

This application is a Continuation of application Ser. No. 11/191,497, filed Jul. 28, 2005 now abandoned which is a Continuation-In-Part of application Ser. No. 11/044,667, filed Jan. 27, 2005 now abandoned which also claims the benefit of Provisional Application Ser. No. 60/592,017, filed Jul. 29, 2004.

FIELD OF THE INVENTION

This invention relates to the field of immunological assays for determining the presence and/or quantifying the amount of taxol in human biological fluids in order to rapidly determine optimal drug concentrations during chemotherapy.

BACKGROUND OF THE INVENTION

Cancer is a term used to describe a group of malignancies that all share the common trait of developing when cells in a part of the body begin to grow out of control. Most cancers form as tumors, but can also manifest in the blood and circulate through other tissues where they grow. Cancer malignancies are most commonly treated with a combination of surgery, chemotherapy, and/or radiation therapy. The type of treatment used to treat a specific cancer depends upon several factors including the type of cancer malignancy and the stage during which it was diagnosed.

Taxol, also known as paclitaxel, is one of the more common cytotoxic agents used for the treatment of Breast (Holmes et. al. Proc. Am. Soc. Clin. Oncol., 10, 60, 1991), Ovarian (Einzig et. al. Proc. Am. Assoc. Cancer Res., 31, 1114, 1990) and non-small cell lung cancer. Taxol has the formula:

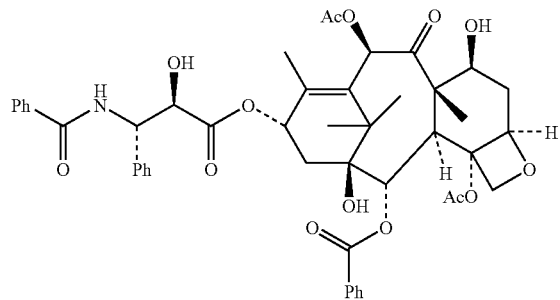

I

This compound has been associated with debilitating side effects such as bone marrow density loss, allergic reaction, neutropenia, hypotension, bardycardia, nausea and vomiting. By monitoring the levels of taxol in the body and adjusting the dose these side effects can be better controlled and limited in patients.

At the same time, there is often highly variable relationship between the dose of taxol and the resulting serum drug concentration that affects therapeutic effect. The degree of intra- and inter-individual pharmacokinetic variability of taxol can be as high as 5-fold (Gurney et. al., J. Clin. Oncol. 14, pp 2590–2611, 1996) and is impacted by many factors, including:

Organ function

Genetic regulation

Disease state

Age

Drug-drug interaction

Time of drug ingestion,

Mode of drug administration, and

Technique-related administration.

As a result of this variability, equal doses of the same drug in different individuals can result in dramatically different clinical outcomes (Hon et. al. *Clinical Chemistry* 44, pp 388–400, 1998). The effectiveness of the same taxol dosage varies significantly based upon individual drug clearance and the ultimate serum drug concentration in the patient. Therapeutic drug management would provide the clinician with insight on patient variation in both oral and intravenous drug administration. With therapeutic drug management, drug dosages could be individualized to the patient, and the chances of effectively treating the cancer, without the unwanted side effects, would be much higher.

In addition, therapeutic drug management of taxol would serve as an excellent tool to ensure compliance in administering chemotherapy with the actual prescribed dosage and achievement of the effective serum concentration levels. It has been found that variability in serum concentration is not only due to physiological factors, but can also result from variation in administration technique.

Routine therapeutic drug management of taxol would require the availability of simple automated tests adaptable to general laboratory equipment. Tests that best fit these criteria are immunoassays. A radioimmunoassay and an enzyme-linked immunosorbent assay) ELISA assay have been reported for taxol (Erlanger et. al. U.S. Pat. No. 5,756,301, May 26, 1998). However the derivatives and immunogens used in this assay impart to the corresponding antibodies a broad cross-reactivity to taxol, and taxol metabolites, particularly, 6-α-hydroxypaclitaxel. In order to be most effective in monitoring drug levels the antibody should be most specific to the active compound and display very low cross-reactivity to no cross-reactivity to the nonactive metabolites.

SUMMARY OF INVENTION

In accordance with this invention, a new class of antibodies have been produced which are substantially selectively reactive to taxol so as to bind to taxol without any substantial cross reactivity to taxol metabolites, particularly 6-α-hydroxypaclitaxel and 3'-p-hydroxypaclitaxel. By selectively reactive it is meant that this antibody only reacts with the taxol molecule and does not substantially react with other compounds such as taxol metabolites the most important blocking metabolites being 6-α-hydroxypaclitaxel and 3'-p-hydroxypaclitaxel.

It has been found that by using immunogens which are conjugates of an immunogenic polyamine polymer with a compound of the formula:

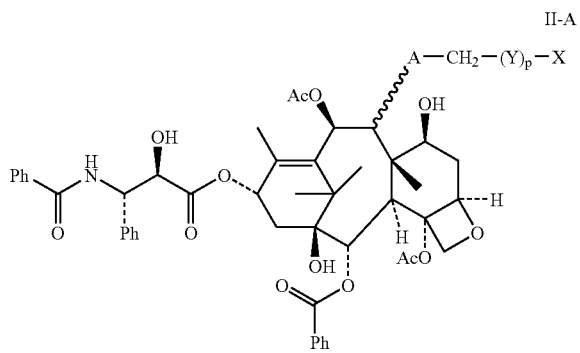

wherein A is

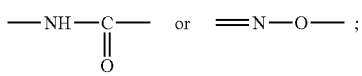

Y is an organic spacing group;
X is a terminal functional group capable of binding to a polyamine polymer;
p is an integer from 0 to 1; and
Ph is phenyl or compounds of the formula:

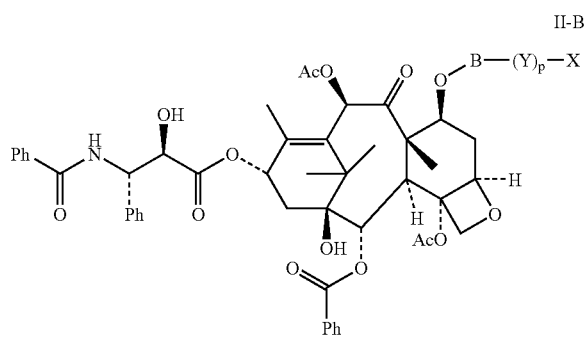

wherein Ph, p, Y and X are as above and B is

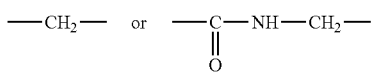

or mixtures thereof; produce antibodies which are specific for taxol and do not substantially react with or bind to other compounds such as metabolites or related compounds of taxol, such as Baccatin III, 3'-p-hydroxypaclitaxel, and 6-α-hydroxypaclitaxel. The provision of these antibodies which substantially selectively react with taxol and do not cross react with 6-α-hydroxypaclitaxel and 3'-p-hydroxypaclitaxel allows one to produce an immunoassay which can specifically detect and monitor taxol in the fluid samples of patients being treated with taxol. Also included within this invention are reagents and kits for said immunoassay. The presence of 6-α-hydroxypaclitaxel and 3'-p-hydroxypaclitaxel as metabolites of taxol is the major cause for false positive readings in past immunoassays for taxol.

DETAILED DESCRIPTION

In accordance with this invention, a new class of antibodies is provided which substantially selectively reacts with taxol and do not substantially react or cross react with taxol metabolites mentioned hereinabove. It has been discovered that through the use of these derivatives of 9-carbonyl taxol of formula II-A and/or of the 7-hydroxy taxol of formula II-B or mixtures thereof; as immunogens, this new class of antibodies of this invention are provided. It is through the use of these antibodies that an immunoassay, including reagents and kits for such immunoassay for detecting and/or quantifying taxol in blood, plasma or other body fluid samples has been developed. By use of this immunoassay, the presence and amount of taxol in body fluid samples, preferable a blood or plasma sample, can be detected and/or quantified. In this manner, a patient being treated with taxol can be monitored during therapy and his treatment adjusted in accordance with said monitoring. By means of this invention one achieves the therapeutic drug management of taxol in cancer patients being treated with taxol as a chemotherapeutic agent.

The reagents utilized in the assay of this invention are conjugates of a polymeric carrier with the compounds of formula II-A and II-B or mixtures thereof. These conjugates are competitive binding partners with the taxol present in the sample for the binding with the antibodies of this invention. Therefore, the amount of conjugate reagent which binds to the antibody will be inversely proportional to the amount of taxol in the sample. In accordance with this invention, the assay utilizes any conventional measuring means for detecting and measuring the amount of said conjugate which is bound or unbound to the antibody. Through the use of said means, the amount of the bound or unbound conjugate can be determined. Generally, the amount of taxol in a sample is determined by correlating the measured amount of the bound or unbound conjugate produced by the taxol in the sample with values of the bound or unbound conjugate determined from standard or calibration curve samples containing known amounts of taxol, which known amounts are in the range expected for the sample to be tested. These studies for producing calibration curves are determined using the same immunoassay procedure as used for the sample.

The conjugates, as well as the immunogens, are prepared from compounds of the formula II-A or II-B or mixtures thereof. The conjugates or immunogens of the carrier are linked to the polyamine polymer ligand portions which have the formula:

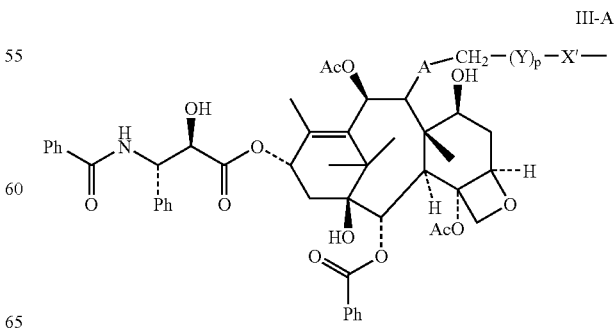

wherein Y, A and p are as above; and
x' is —CH$_2$— or a functional linking group;
compounds of the formula:

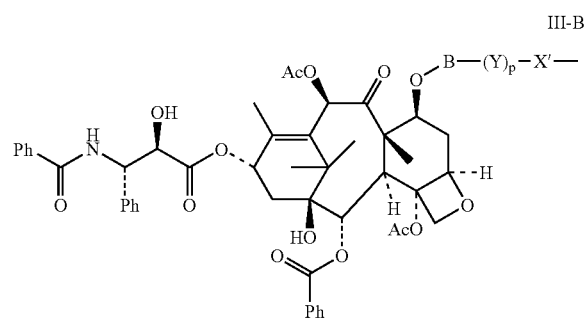

III-B wherein x', A, B and p are as above.

These ligand portions may be linked to one or more active sites on the carrier or polyamine polymer of the immunogen.

Definitions

Throughout this description the following definitions are to be understood:

The term "Ph" as used throughout this application designates a phenyl radical. The term "alkylene" designates a divalent saturated straight or branch chain hydrocarbon substituent containing from one to ten carbon atoms The terms "immunogen" and "immunogenic" refer to substances capable of eliciting, producing, or generating an immune response in an organism.

The term "conjugate" refers to any substance formed from the joining together of two parts. Representative conjugates in accordance with the present invention include those formed by the joining together of a small molecule, such as the compound of formula II-A and II-B, and a large molecule, such as a carrier or a polyamine polymer, particularly protein. In the conjugate the small molecule maybe joined at one or more active sites on the large molecule. The term conjugate includes the term immunogen.

"Haptens" are partial or incomplete antigens. They are protein-free substances, mostly low molecular weight substances, which are not capable of stimulating antibody formation, but which do react with antibodies. The latter are formed by coupling a hapten to a high molecular weight immunogenic carrier and then injecting this coupled product, i.e., immunogen, into a human or animal subject. The hapten of this invention is taxol.

As used herein, a "spacing group" or "spacer" refers to a portion of a chemical structure which connects two or more substructures such as haptens, carriers, immunogens, labels, or tracers through a CH2 or functional linking group. These spacer groups will be enumerated hereinafter in this application. The atoms of a spacing group and the atoms of a chain within the spacing group are themselves connected by chemical bonds. Among the preferred spacers are straight or branched, saturated or unsaturated, carbon chains. Theses carbon chains may also include one or more heteroatoms within the chain or at termini of the chains. By "heteroatoms" is meant atoms other than carbon which are chosen from the group consisting of oxygen, nitrogen and sulfur. Spacing groups may also include cyclic or aromatic groups as part of the chain or as a substitution on one of the atoms in the chain.

The number of atoms in the spacing group is determined by counting the atoms other than hydrogen. The number of atoms in a chain within a spacing group is determined by counting the number of atoms other than hydrogen along the shortest route between the substructures being connected. A functional linking group may be used to activate, e.g., provide an available functional site on, a hapten or spacing group for synthesizing a conjugate of a hapten with a label or carrier or polyamine polymer.

An "immunogenic carrier," as the terms are used herein, is an immunogenic substance, commonly a protein, that can join with a hapten, in this case taxol or the taxol derivatives hereinbefore described, thereby enabling these hapten derivatives to induce an immune response and elicit the production of antibodies that can bind specifically with these haptens. The immunogenic carriers and the linking groups will be enumerated hereinafter in this application. Among the immunogenic carrier substances are included proteins, glycoproteins, complex polyamino-polysaccharides, particles, and nucleic acids that are recognized as foreign and thereby elicit an immunologic response from the host. The polyamino-polysaccharides may be prepared from polysaccharides using any of the conventional means known for this preparation.

Also various protein types may be employed as a poly (amino acid) immunogenic carrier. These types include albumins, serum proteins, lipoproteins, etc. Illustrative proteins include bovine serum albumin (BSA), keyhole limpet hemocyanin (KLH), egg ovalbumin, bovine thyroglobulin (BTG) etc. Alternatively, synthetic poly(amino acids) may be utilized.

Immunogenic carriers can also include poly amino-polysaccharides, which are a high molecular weight polymer built up by repeated condensations of monosaccharides. Examples of polysaccharides are starches, glycogen, cellulose, carbohydrate gums such as gum arabic, agar, and so forth. The polysaccharide also contain polyamino acid residues and/or lipid residues.

The immunogenic carrier can also be a poly(nucleic acid) either alone or conjugated to one of the above mentioned poly(amino acids) or polysaccharides.

The immunogenic carrier can also include solid particles. The particles are generally at least about 0.02 microns (μm) and not more than about 100 μm, and usually about 0.05 μm to 10 μm in diameter. The particle can be organic or inorganic, swellable or non-swellable, porous or non-porous, optimally of a density approximating water, generally from about 0.7 to 1.5 g/mL, and composed of material that can be transparent, partially transparent, or opaque. The particles can be biological materials such as cells and microorganisms, including non-limiting examples such as erythrocytes, leukocytes, lymphocytes, hybridomas, *Streptococcus, Staphylococcus aureus, E. coli*, and viruses. The particles can also be comprised of organic and inorganic polymers, liposomes, latex, phospholipid vesicles, or lipoproteins.

"Poly(amino acid)" or "polypeptide" is a polyamide formed from amino acids. Poly(amino acids) will generally range from about 2,000 molecular weight, having no upper molecular weight limit, normally being less than 10,000,000 and usually not more than about 600,000 daltons. There will usually be different ranges, depending on whether an immunogenic carrier or an enzyme is involved.

A "peptide" is any compound formed by the linkage of two or more amino acids by amide (peptide) bonds, usually a polymer of α-amino acids in which the α-amino group of each amino acid residue (except the NH$_2$ terminus) is linked to the α-carboxyl group of the next residue in a linear chain. The terms peptide, polypeptide and poly(amino acid) are used synonymously herein to refer to this class of compounds without restriction as to size. The largest members of this class are referred to as proteins.

A "label," "detector molecule," or "tracer" is any molecule which produces, or can be induced to produce, a detectable signal. The label can be conjugated to an analyte, immunogen, antibody, or to another molecule such as a receptor or a molecule that can bind to a receptor such as a ligand, particularly a hapten. Non-limiting examples of labels include radioactive isotopes, enzymes, enzyme fragments, enzyme substrates, enzyme inhibitors, coenzymes, catalysts, fluorophores, dyes, chemiluminescers, luminescers, or sensitizers; a non-magnetic or magnetic particle, a solid support, a liposome, a ligand, or a receptor.

The term "antibody" refers to a specific protein binding partner for an antigen and is any substance, or group of substances, which has a specific binding affinity for an antigen to the exclusion of other substances. The generic term antibody subsumes polyclonal antibodies, monoclonal antibodies and antibody fragments.

The term "derivative" refers to a chemical compound or molecule made from a parent compound by one or more chemical reactions.

The term "carrier" refers to solid particles and/or polymeric polymers such as immunogenic polymers such as those mentioned above. Where the carrier is a solid particle, the solid particle may be bound, coated with or otherwise attached to a polyamine polymer to provide one or more reactive sites for bonding to the terminal functional group X in the compounds of the formula II-A and II-B.

The term "reagent kit," or "test kit," refers to an assembly of materials that are used in performing an assay. The reagents can be provided in packaged combination in the same or in separate containers, depending on their cross-reactivities and stabilities, and in liquid or in lyophilized form. The amounts and proportions of reagents provided in the kit can be selected so as to provide optimum results for a particular application. A reagent kit embodying features of the present invention comprises antibodies specific for Taxol. The kit may further comprise ligands of the analyte and calibration and control materials. The reagents may remain in liquid form or may be lyophilized.

The phrase "calibration and control materials" refers to any standard or reference material containing a known amount of a drug to be measured. The concentration of drug is calculated by comparing the results obtained for the unknown specimen with the results obtained for the standard. This is commonly done by constructing a calibration curve.

The term "biological sample" includes, but is not limited to, any quantity of a substance from a living thing or formerly living thing. Such living things include, but are not limited to, humans, mice, monkeys, rats, rabbits, horses, and other animals. Such substances include, but are not limited to, blood, serum, plasma, urine, cells, organs, tissues, bone, bone marrow, lymph, lymph nodes, synovial tissue, chondrocytes, synovial macrophages, endothelial cells, and skin.

Reagents and Immunogens

In constructing an immunoassay, a conjugate of taxol is constructed to compete with the taxol in the sample for binding sites on the antibodies. In the immunoassay of this invention, the reagents are the 9-substituted taxol derivatives of the compounds of formula III-A and the 7-taxol derivatives of formula III-B. In the compounds of formula III-A and III-B, the linker spacer constitutes the —CH$_2$—(Y)$_p$—X'— or —B—(Y)$_p$—X' portion of this molecule. These linker X' and the spacer —CH$_2$—(Y)$_p$— or —B—(Y)$_p$—X' are conventional in preparing conjugates and immunogens. Any of the conventional spacer-linking groups utilized to prepare conjugates and immunogens for immunoassays can be utilized in the compounds of formula III-A and III-B. Such conventional linkers and spacers are disclosed in U.S. Pat. No. 5,501,987 and U.S. Pat. No. 5,101,015.

Among the preferred spacer groups are included the spacer groups hereinbefore mentioned. Particularly preferred spacing groups are groups such as alkylene containing from 1 to 10 carbon atoms,

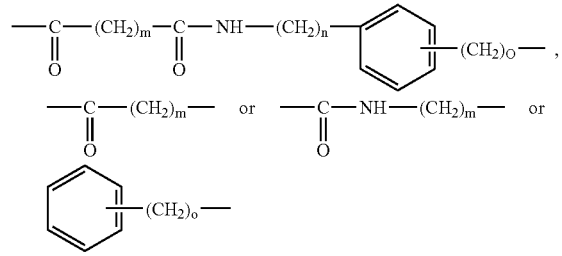

wherein n and o are integers from 0 to 6, and m is an integer from 1 to 6 with alkylene being the especially preferred spacing group.

In the compounds of formula III-A and III-B, X' is —CH$_2$— or a functional group linking the spacer, preferably to an amine group on the polymeric carrier. The group X' is the result of the terminal functional group X in the compounds of Formula II-A and II-B which is capable of binding to the amino group in the polyamine polymer used as either the carrier or the immunogen. Any terminal functional group capable of reacting with an amine can be utilized as the functional group X in the compounds of formula II-A and II-B. These terminal functional groups preferably included within X are:

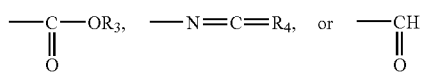

wherein R$_3$ is hydrogen or taken together with its attached oxygen atom forms a reactive ester and R$_4$ is oxygen or sulfur. The radical —N=C=R$_4$, can be an isocyanate or as isothiocyanate. The active esters formed by OR$_3$ include imidoester, such as N-hydroxysuccinamide, 1-hydroxy benzotriazole and p-nitrophenyl ester. However any active ester which can react with an amine group can be used.

The carboxylic group and the active esters are coupled to the carrier or immunogenic polymer by conventional means. The amine group on the polyamine polymer, such as a protein, produces an amide group which connects the spacer to the polymer, immunogens or carrier and/or conjugates of this invention.

In the immunogens and conjugates of the present invention, the chemical bonds between the carboxyl group-containing taxol haptens and the amino groups on the polyamine polymer on the carrier or immunogen can be established using a variety of methods known to one skilled in the art. It is frequently preferable to form amide bonds. Amide bonds are formed by first activating the carboxylic acid moiety of the taxol hapten in the compounds of formula II-A and II-B by reacting the carboxy group with a leaving group reagent (e.g., N-hydroxysuccinimide, 1-hydroxybenzotriazole, p-nitrophenol and the like). An activating reagent such as dicyclohexylcarbodiimide, diisopropylcarbodiimide and the like can be used. The activated form of the carboxyl group in the taxol hapten of formula II-A or II-B is then reacted with a buffered solution containing the protein carrier.

In cases where the taxol derivative of formula II-A or II-B contains a primary or secondary amino group as well as the carboxyl group, it is necessary to use an amine protecting group during the activation and coupling reactions to prevent the conjugates from reacting with themselves. Typically, the amines on the conjugate are protected by forming the corresponding N-trifluoroacetamide, N-tertbutyloxycarbonyl urethane (N-t-BOC urethane), N-carbobenzyloxy urethane or similar structure. Once the coupling reaction to the immunogenic polymer or carrier has been accomplished, as described above, the amine protecting group can be removed using reagents that do not otherwise alter the structure of the immunogen or conjugate. Such reagents and methods are known to one skilled in the art and include weak or strong aqueous or anhydrous acids, weak or strong aqueous or anhydrous bases, hydride-containing reagents such as sodium borohydride or sodium cyanoborohydride and catalytic hydrogenation. Various methods of conjugating haptens and carriers are also disclosed in U.S. Pat. No. 3,996,344 and U.S. Pat. No. 4,016,146, which are herein incorporated by reference.

On the other hand where X is a terminal isocyanate or thioisocyanate radical in the compound of formula II-A or II-B, these radicals when reacted with the free amine of a polyamine polymer produce the conjugate or immunogen of formula III-A or III-B where X' is

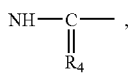

where $R_4$ is as above, which functionally connects with the amino group on the polyamine carrier or the immunogenic polypeptide.

Where X, in the compounds of formula II-A and II-B, is an aldehyde group these compounds may be connected to the amine group of the polyamine polypeptide or carrier through an amine linkage by reductive amination. Any conventional method of condensing an aldehyde with an amine such as through reductive amination can be used to form this linkage. In this case, X' in the ligand portions of formula III-A and III-B is —CH$_2$—.

Taxol of the compound of formula I and its 9-keto group can be represented by the formula:

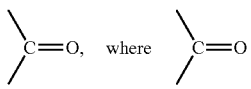

represents taxol with its 9-keto group shown. The 9-keto taxol can be connected to the compound of formula II-A where A is =N—O— by reacting taxol with a methoxyamine of the formula:

$$NH_2—O—CH_2—(Y)_p—X \qquad \text{V-A}$$

to produce the compound of the formula:

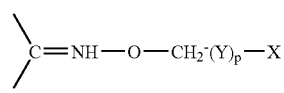

wherein p, Y and X are as above.

The compound of formula I is reacted at its 9-oxo group with a methoxyamine of formula V-A to form the compounds of formula VI-A by conventional means of condensing methoxyamine with a carbonyl group to form an oxylamine of formula VI-A such as disclosed in U.S. Pat. No. 4,039,385. If the compound of formula V-A contains any reactive amino or other functional substituents, these substituents can be reacted with conventional protecting groups prior to the reaction of taxol with a compound of V-A. After the compound of formula VI-A is produced, these protecting groups can be removed by procedures well known in the art for removing such protecting groups while retaining the oxylamine linkage in the compound of formula VI-A.

The compound of formula II-A where A is

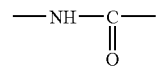

can be prepared by first converting the 9-oxo group on taxol to 9-amino group and then condensing this 9-amino taxol with an acid halide of the formula:

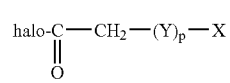

wherein Y, p and X are as above.

The 9-oxo group on taxol can be converted to the 9-amino group by reductive amination utilizing ammonium chloride and a reducing agent such as sodium cyanoborohydride.

Any of the conditions conventional in reductive amination can be utilized to convert the 9-oxo group on taxol to an amine group. The 9-amino taxol is reacted with the acid halide by condensation to form the amide of formula II-A where A is

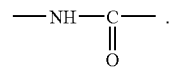

Any method of condensing an acid halide with an amine to form an amide can be utilized to carry out his condensation.

The 7-substituted compounds of formula II-B where B is —CH$_2$— is formed by reacting the 7-hydroxy group of taxol with a halide of the formula:

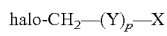   V-C wherein p, Y and X are as above.

forming the compound of formula II-B from taxol, any conventional means of reacting an alcohol to form an ether can be utilized in condensing the compound of formula V-C with the 7-hydroxy position on the taxol. The use of a halide in the compound of formula V-C provides an efficient means for forming such an ether by condensing with the alcohol. On the other hand, where the compound of formula V-C contains functional groups, which may interfere with this reaction to form the compound of formula II-B, these functional groups can be protected by means of suitable protecting groups which can be removed after this reaction as described hereinabove.

The 7-substituted compounds of formula II-B where B is

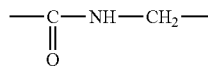

is produced by reacting 7-hydroxy group on taxol with an amino compound of the formula:

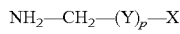   VI wherein X, Y and p are as above.

After first converting the 7-hydroxy group on taxol to the chloroformatic group

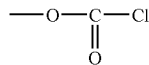

Any conventional means of converting a hydroxy group to a chloroformatic group can be used. After the formulation of a chloroformate, the halo group of the chloroformate is condensed with the amine group in the compound of formula VI. Prior to this reaction, the reactive group on taxol and/or on the compound of formula VI are protected as described hereinabove with a conventional protecting group. These protecting groups can be removed after this halide condensation by conventional means such as described hereinbefore.

The compound of formula II-A and II-B can be converted into the immunogens and/or the conjugate reagents of this invention by reacting these compounds with a polyamine or a polypeptide. The same polypeptide can be utilized as the carrier and as the immunogenic polymer in the immunogen of this invention provided that polyamine or polypeptide is immunologically active. However, to form the conjugates, these polymers need not produce an immunological response as needed for the immunogens. In accordance with this invention, the various functional group represented by X in the compounds of formula II-A and II-B can be conjugated to the polymeric material by conventional means of attaching a functional group to an amine group contained within the polymer. In accordance with a preferred embodiment, in the compound of formula II-A and II-B, X is a carboxylic acid group.

Antibodies

The present invention also relates to novel antibodies including monoclonal antibodies to taxol produced by utilizing the aforementioned immunogens. In accordance with this invention it has been found that these antibodies produced in accordance with this invention are selectively reactive with taxol and unlike the prior art antibodies, do not react with metabolites which would interfere with immunoassays for taxol. The most problematic of these taxol metabolites are 6-α-hydroxypaclitaxel and 3'-p-hydroxypaclitaxel. The ability of the antibodies of this invention not to react with these 6-α-hydroxypaclitaxel and 3'-hydroxypaclitaxel metabolites makes these antibodies particularly valuable in providing an immunoassay for taxol.

The present invention relates to novel antibodies and monoclonal antibodies to taxol. The antisera of the invention can be conveniently produced by immunizing host animals with the immunogens of this invention. Suitable host animals include rodents, such as, for example, mice, rats, rabbits, guinea pigs and the like, or higher mammals such as goats, sheep, horses and the like. Initial doses, bleedings and booster shots can be given according to accepted protocols for eliciting immune responses in animals, e.g., in a preferred embodiment mice received an initial dose of 100 ug immunogen/mouse, i.p. and two or more subsequent booster shots of between 50 and 100 ug immunogen/mouse over a six month period. Through periodic bleeding, the blood samples of the immunized mice were observed to develop an immune response against taxol binding utilizing conventional immunoassays. These methods provide a convenient way to screen for hosts which are producing antisera having the desired activity. The antibodies were also screened against the major metabolites of taxol and showed no substantial binding to these compounds.

Monoclonal antibodies are produced conveniently by immunizing Balb/c mice according to the above schedule followed by injecting the mice with 100 ug immunogen i.p. or i.v. on three successive days starting four days prior to the cell fusion. Other protocols well known in the antibody art may of course be utilized as well. The complete immunization protocol detailed herein provided an optimum protocol for serum antibody response for the antibody to taxol.

B lymphocytes obtained from the spleen, peripheral blood, lymph nodes or other tissue of the host may be used as the monoclonal antibody producing cell. Most preferred are B lymphocytes obtained from the spleen. Hybridomas capable of generating the desired monoclonal antibodies of the invention are obtained by fusing such B lymphocytes with an immortal cell line, which is a cell line that which imparts long term tissue culture stability on the hybrid cell. In the preferred embodiment of the invention the immortal cell may be a lymphoblastoid cell or a plasmacytoma cell such as a myeloma cell, itself an antibody producing cell but also malignant. Murine hybridomas which produce Taxol monoclonal antibodies are formed by the fusion of mouse myeloma cells and spleen cells from mice immunized against Taxol-protein conjugates. Chimeric and humanized monoclonal antibodies can be produced by cloning the antibody expressing genes from the hybridoma cells and employing recombinant DNA methods now well known in the art to either join the subsequence of the mouse variable region to human constant regions or to combine human framework regions with complementary determining regions (CDR's) from a donor mouse or rat immunoglobulin. An improved method for carrying out humanization of murine monoclonal antibodies which provides antibodies of enhanced affinities is set forth in International Patent Application WO 92/11018.

Polypeptide fragments comprising only a portion of the primary antibody structure may be produced, which fragments possess one or more immunoglobulin activities. These polypeptide fragments may be produced by proteolytic cleavage of intact antibodies by methods well known in the art, or by inserting stop codons at the desired locations in expression vectors containing the antibody genes using site-directed mutageneses to produce Fab fragments or (Fab')$_2$ fragments. Single chain antibodies may be produced by joining VL and VH regions with a DNA linker (see Huston et al., *Proc. Natl. Acad. Sci. U.S.A.*, 85:5879–5883 (1988) and Bird et al., *Science*, 242:423–426 (1988))

The antibodies of this invention are selective for taxol without having any substantial cross-reactivity with metabolites of taxol such as the metabolites mentioned hereinabove. By having no substantial cross-reactivity it is meant that the antibodies of this invention have a cross reactivity relative to taxol with these metabolites of less than 10%. The antibodies of this invention may be reactive with other taxol like compounds such as docetaxel.

Immunoassays

In accordance with this invention, the conjugates and the antibodies generated from the immunogens of these compounds of formula II-A and II-B or mixtures thereof can be utilized as reagents for the determination of taxol in patient samples. This determination is performed by means of an immunoassay. Any immunoassay in which the reagent conjugates formed from the compounds of formula II-A and II-B compete with the taxol in the sample for binding sites on the antibodies generated in accordance with this invention can be utilized to determine the presence of taxol in a patient sample. The manner for conducting such an assay for taxol in a sample suspected of containing taxol, comprises combining an (a) aqueous medium sample, (b) an antibody to taxol generated in accordance with this invention and (c) the conjugates formed from the compounds of formula II-A or II-B or mixtures thereof. The amount of taxol in the sample can be determined by measuring the inhibition of the binding to the specific antibody of a known amount of the conjugate added to the mixture of the sample and antibody. The result of the inhibition of such binding of the known amount of conjugates by the unknown sample is compared to the results obtained in the same assay by utilizing known standard solutions of taxol. In determining the amount of taxol in an unknown sample, the sample, the conjugates formed from the compounds of formula II-A and II-B and the antibody may be added in any order.

Various means can be utilized to measure the amount of conjugate formed from the compounds of formula II-A and II-B bound to the antibody. One method is where binding of the conjugates to the antibody causes a decrease in the rate of rotation of a fluorophore conjugate. The amount of decrease in the rate of rotation of a fluorophore conjugate in the liquid mixture can be detected by the fluorescent polarization technique such as disclosed in U.S. Pat. No. 4,269,511 and U.S. Pat. No. 4,420,568.

On the other hand, the antibody can be coated or absorbed on nanoparticles so that when these particles react with the taxol conjugates formed from the compounds of formula II-A and II-B, these nanoparticles form an aggregate. However, when the antibody coated or absorbed nanoparticles react with the taxol in the sample, the taxol from the sample bound to these nanoparticles does not cause aggregation of the antibody nanoparticles. The amount of aggregation or agglutination can be measured in the assay mixture by absorbance.

On the other hand, these assays can be carried out by having either the antibody or the taxol conjugates attached to a solid support such as a microtiter plate or any other conventional solid support including solid particles. Attaching antibodies and proteins to such solid particles is well known in the art. Any conventional method can be utilized for carrying out such attachments. In many cases, in order to aid measurement, labels may be placed upon the antibodies, conjugates or solid particles, such as radioactive labels or enzyme labels, as aids in detecting the amount of the conjugates formed from the compounds of formula II-A and II-B which is bound or unbound with the antibody. Other suitable labels include chromophores, fluorophores, etc.

As a matter of convenience, assay components of the present invention can be provided in a kit, a packaged combination with predetermined amounts of new reagents employed in assaying for taxol. These reagents include the antibody of this invention, as well as, the conjugates formed from the compounds of formula II-A and II-B or mixtures thereof. It is generally preferred that in a given immunoassay, if a conjugate formed from a compound of formula II-A is utilized, that the antibody be generated by an immunogen formed from a compound of formula II-A. In a like manner, if a conjugate formed from a compound of formula II-B is utilized, the antibody be generated by the immunogen formed from a compound of formula II-B. However, this need not be the case and antibodies and conjugates in a given assay can be derived from either or both of these conjugates and immunogens.

In addition to these necessary reagents, additives such as ancillary reagents may be included, for example, stabilizers, buffers and the like. The relative amounts of the various reagents may vary widely to provide for concentrations in solution of the reagents which substantially optimize the sensitivity of the assay. Reagents can be provided in solution or as a dry powder, usually lyophilized, including excipients which on dissolution will provide for a reagent solution having the appropriate concentrations for performing the assay.

EXAMPLES

In the examples, Ph represents phenyl. In the examples, the following abbreviations are used for designating the following:
THF Tetrahydrofuran
EA Ethyl alcohol
EtOAc Ethyl Acetate
DCM Dichloromethane
DMAP Dimethylaminopyridine
NHS N-hydroxy succinimide
EDC 1-(3-dimethylaminopropyl)-3-ethylcarbodiimide hydrochloride
TLC Thin Layer Chromatrography
ANS 8-Anilino-1-naphthalenesulfonic acid
i.p. Intraperitoneal
HRP horse radish-peroxidase
TMB 3,3',5,5'-Tetramethylbenzidine
TRIS Tris(hydroxymethyl)aminomethane hydrochloride
BSA Bovine serum albumin
BTG Bovine thyroglobulin
PBS Phosphate buffered saline
di deionized water In the examples, Scheme 1 and Scheme 2 below set forth the specific compounds prepared and referred to by numbers in the Examples. The schemes are as follows:

Scheme 1
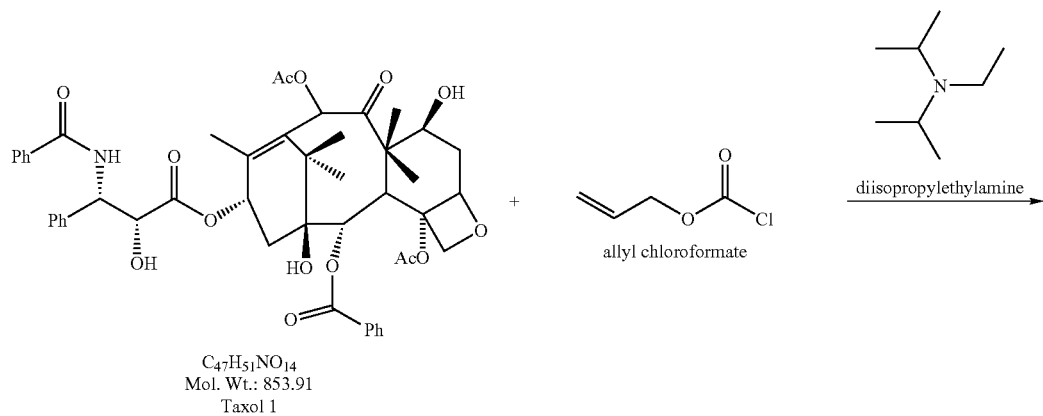
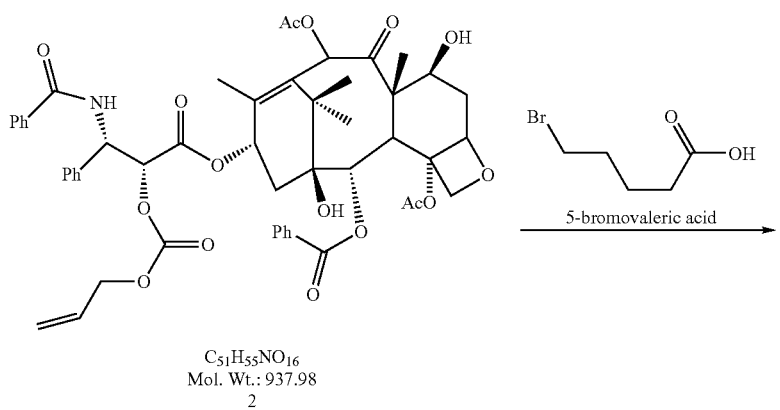
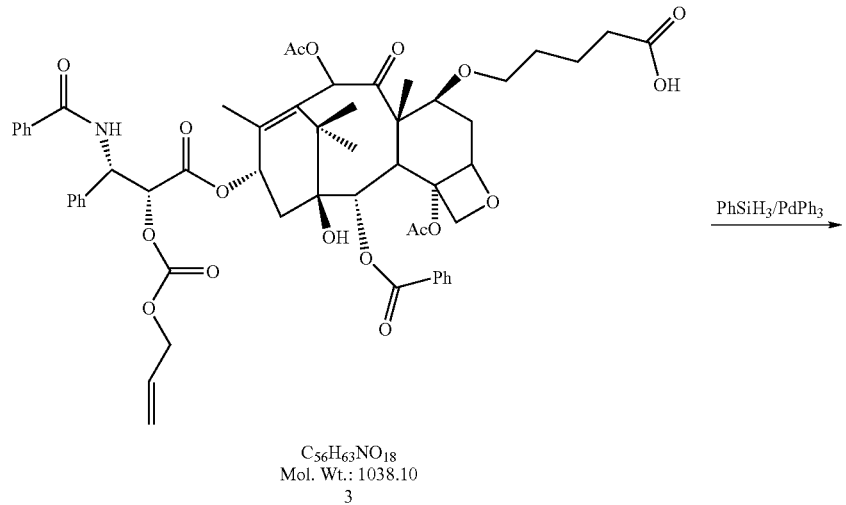

-continued
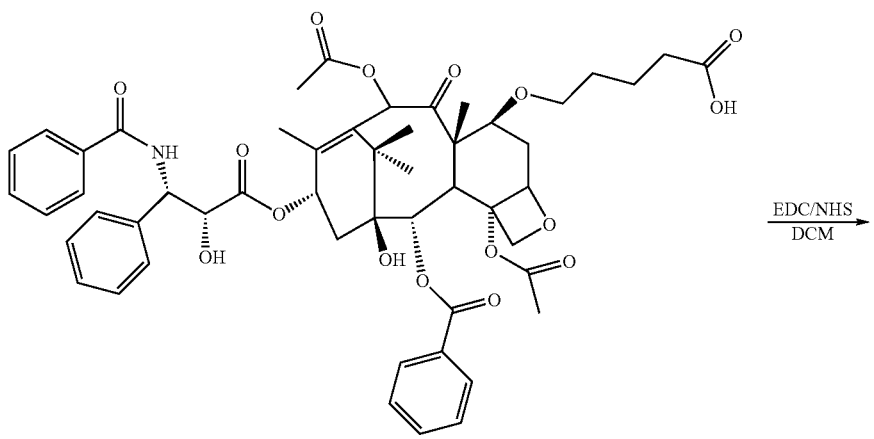
C$_{54}$H$_{59}$NO$_{16}$
Exact Mass: 953.38
Mol. Wt.: 954.02
4
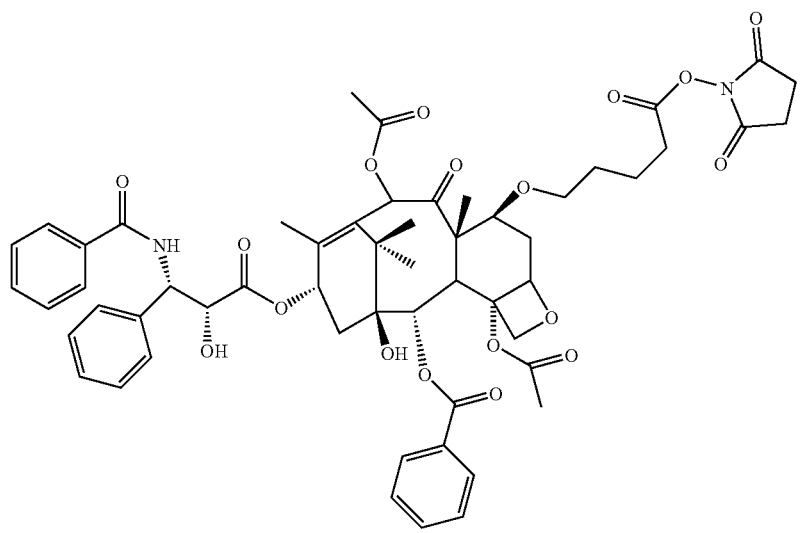
C$_{56}$H$_{62}$N$_2$O$_{18}$
Exact Mass: 1050.40
Mol. Wt.: 1051.09
5
Scheme 2
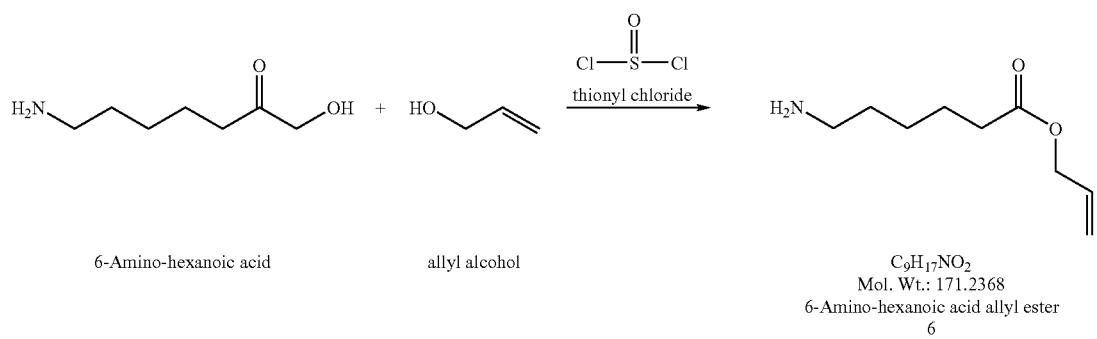
6-Amino-hexanoic acid     allyl alcohol
C$_9$H$_{17}$NO$_2$
Mol. Wt.: 171.2368
6-Amino-hexanoic acid allyl ester
6

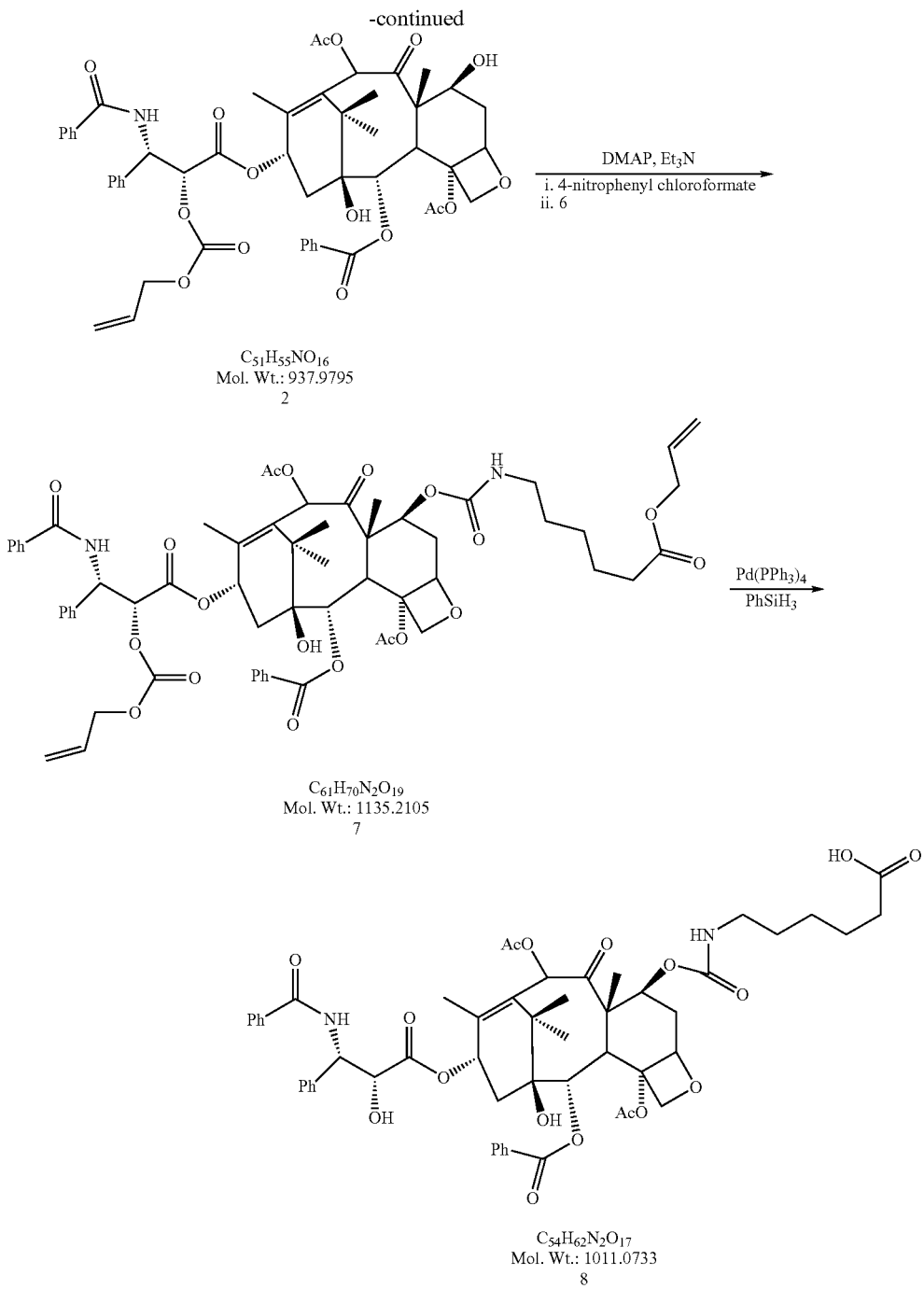

Example 1

Preparation of Taxol Derivative [5] (Scheme 1)

Taxol 1 (1.685 g) was placed in a three-neck flask in 26 mL of freshly distilled dichloromethane, under continuous flow of argon. During this addition the temperature was maintained at −15° C., and diisopropylamine (1 eq.) and allyl chloroformate (1.1 eq.) were also added. The reaction mixture temperature was brought to room temperature and allowed to stir for 4 hours. After this time 40 mL of dichloromethane was added and reaction mixture was washed with 0.1N HCl (60 mL), dried on $Na_2SO_4$, and concentrated on a rotavap to produce the product 2 where the 2' hydroxy group on taxol was protected. This product was left in a desiccator for 2 days and then was used in the next step and in Example 2 without further purification.

The product 2 was then dissolved in 40 mL of THF under argon while the temperature was maintained at −15° C. Then to this solution, first NaH (2 eq.) was added and after 10 minutes, 5-bromo valeric acid (1.1 eq dissolved in 3 mL of THF and added slowly) to produce 3 as a product in the reaction mixture. After TLC confirmation of the product 3, 4.4 mL of 2 N HCl was added drop wise to this reaction mixture. The reaction mixture containing the product 3 was washed with water, dried on $Na_2SO_4$, concentrated on a rotavap and then purified.

The product 3 was purified on silica gel column, eluted with 15% EtOAc:DCM to 20% EtOAc:DCM, yielding 1.1611 g of the pure product 3.

The purified product 3 was dissolved in 40 mL of dichloromethane under argon and then $PhSiH_3$ (6.25 eq.) was added to this solution along with $Pd(PPh_3)_4$ (0.05 eq.). The resulting reaction mixture was allowed to stand for 1 hour. After which time, 12 mL of MeOH was added to the reaction mixture and the resulting reaction mixture was stirred for 10 minutes. This reaction mixture was evaporated to dryness to produce the product 4 with the deprotected 2' hydroxy group.

The product 4 was purified from the reaction mixture on a silica gel column using 30% EtOAc:DCM as solvent system and isolated as an off white powder (817 mg, 43.4% by weight yield from starting material).

The purified product 4 (355 mg, 0.37 mmol) was dissolved in 15 mL of dichloromethane. Then N-hydroxy succinimide (2 eq.) and EDC (2 eq.) were added under argon and the resulting reaction mixture was allowed to stir overnight. The reaction mixture containing the product 5 was washed with 0.1 N HCl and then with $H_2O$ as quickly as possible. The reaction mixture containing the product 5 was dried on $Na_2SO_4$, and concentrated on a rotavap under high vacuum to yield 401 mg (99.9% purity) of product 5.

Example 2

Preparation of Taxol Derivative [8] Scheme 2

To a suspension of 6-aminohexanoic acid (3 g, 22.87 mmol) in allyl alcohol (14 mL, excess) was added thionyl chloride slowly. The reaction mixture was stirred at room temperature overnight to produce 4-aminohexanoic acid allyl ester 6. After removal of excess allyl alcohol, the product 4-aminohexanoic acid allyl ester (3.9 g, white crystalline solid) was dried under high vacuum.

To a solution of allyl-protected taxol product 2 produced in Example 1, (400 mg, 0.43 mmol) and DMAP (191.5 mg, 1.57 mmol) in DCM (10 mL) under nitrogen there was added triethylamine (1.57 mmol) followed by p-nitrophenyl chloroformate (103 mg, 0.51 mmol). The reaction mixture was then stirred at room temperature for 5.5 hours and then a solution of amine 6, prepared above, as a white crystalline solid (1.1 eq) dissolved in DCM (2 mL) was added to form the product 7. This resulting mixture was allowed to stir overnight at room temperature. From this resulting reaction mixture, the DCM was removed under vacuum and the crude reaction product 7 was purified on silica gel column with 15% EtOAc/DCM as the solvent system to yield the purified product 7 (320 mg, 66.1%) as an off-white solid.

The purified product 7, prepared above, was dissolved in 30 mL of dichloromethane under argon and then $PhSiH_3$ (6.25 eq.) was added along with $Pd(PPh_3)_4$ (0.05 eq.). After 1.5 hours, 12 mL of MeOH was added and stirred for an additional 10 minutes. Reaction mixture was evaporated to dryness to produce the derivatized 7-hydroxy taxol product 8. This product 8 was purified on silica gel column (10% MeOH:EtOAc as solvent system) and isolated as an off white gum (236 mg, 82.8%), 54.73% yield from starting material.

Example 3

Preparation of Taxol Immunogen

To 6.8 mL of BTG (36.4 mg/mL) in 50 mM phosphate buffer (50 mM, pH 7.5) dimethyl sulfoxide (DMSO) (13.8 mL) was added dropwise to form a solution. To 16.6 mL of this solution, the purified activated N-Hydroxysuccinimide ester taxol derivative 5 prepared in Example 1 (1.26 mL of a 50 mg/mL in DMSO solution) was added drop wise. The resulting mixture was allowed to stir overnight at room temperature to conjugate the BTG to the purified taxol derivative 5. This immunogenic conjugate was then purified by dialysis and characterized according to procedures described previously (Wu et. al., Bioconj. Chem., 8: pp 385–390, 1997, Li et. al., Bioconj. Chem., 8: pp 896–905, 1997, Salamone et. al., J. Forensic Sci. pp 821–826, 1998).

Example 4

Preparation of Taxol Antibodies

Ten Female BALB/c mice were immunized i.p. with 100 μg/mouse of taxol-BTG (prepared in Example 3) emulsified in Complete Freund's Adjuvant. Mice were boosted once four weeks after the initial injection with 100 μg taxol-BTG/mouse emulsified in Incomplete Freund's Adjuvant. Ten days after the boost, test bleeds from each mouse were obtained by orbital bleed. The anti-serum from these test bleeds contained taxol antibodies evaluated in Examples 7, 8a and 9. For monoclonal antibodies, starting four days before the fusion, the mice were injected i.p. with 100 μg of taxol-BTG in PBS on three successive days. Spleen cells were isolated from the selected mice and fused with $2 \times 10^7$ myeloma cells SP2/0 with 50% polyethylene glycol 1500 according to the method of Coligan, J. E. et al., eds., *Current Protocols in Immunology*, 2.5.1–2.5.8, (1992), Wiley & Sons, NY. The fused cells were plated on ten 96-well plates in DMEM/F12 supplemented with 20% FetalClone I, 2% L-glutamine (100 mM) and 2% 50×HAT. Two weeks later, the hybridoma supernatant was assayed for the presence of anti-taxol-BTG antibodies by ELISA (example 8b). Cells from the wells that gave positive ELISA results (example 8b) were expanded to 24 well plates. Clones positive by ELISA were subcloned once or twice by limiting dilution according to the method disclosed in Coligan, J. E. et al., eds., *Current Protocols in Immunology*, 2.5.8–2.5.17, (1992), Wiley & Sons, NY. Hybridoma culture supernatants containing monoclonal antibody from selected subclones were confirmed for taxol binding by a competitive ELISA (examples 8a and 9). These monoclonal antibodies were tested for taxol binding and cross-reactivity to taxol metabolites by indirect competitive microtiter plate assay as described in example 9.

Example 5

Preparation of Taxol-BSA Conjugate with Derivative 5

To a 20 mL solution of BSA (50 mg/mL) in phosphate buffer (50 mM, pH 7.5) 20 mL of dimethyl sulfoxide (DMSO) were added drop wise. To 18 mL of this solution, the activated N-Hydroxysuccinimide ester taxol derivative 5 prepared as in example 1, (0.316 mL of a 50 mg/mL in DMSO solution) was added drop wise. The mixture was allowed to stir overnight at room temperature to produce the conjugate of the activated ester 5 and BSA. This conjugate was then purified by dialysis and characterized according to procedures described previously (Wu et. al., Bioconj. Chem., 8: pp 385–390, 1997, Li et. al., Bioconj. Chem., 8: pp 896–905, 1997, Salamone et. al., J. Forensic Sci. pp 821–826, 1998).

Example 6

Preparation of Taxol-BSA Conjugate with Derivative 8

To 25 mg of the taxol derivative 8, prepared in example 2, in methylene chloride (3 mL), EDC (28 mg) and NHS (16.8 mg) were added. The solution was stirred in a nitrogen atmosphere at room temperature for 24 hours. To this mixture 7 mL of additional methylene chloride were added followed by 2 mL of hydrochloric acid (0.3 N). The reaction mixture was stirred for 15 minutes and the organic layer was separated, dried and evaporated to yield an amorphous white residue which was the NHS activated ester of Taxol derivative 8. This residue was dissolved in 2 mL of DMSO and 1.25 mL of this solution was added drop wise to 40 mL of a BSA solution (25 mg/mL, 20 mL DMSO/20 mL 50 mM phosphate, pH 7.5). The solution was stirred for 60 hours at room temperature to produce the conjugate of BSA and the taxol derivative 8. This conjugate was purified by dialysis according to procedures previously described (Wu et. al., Bioconj. Chem., 8: pp 385–390, 1997, Li et. al., Bioconj. Chem., 8: pp 896–905, 1997, Salamone et. al., J. Forensic Sci. pp 821–826, 1998).

Example 7a

Microtiter Plate Sensitization Procedure with Taxol Derivative 5

The ELISA method for measuring taxol concentrations was performed in polystyrene microtiter plates (Nunc Max-iSorp C8 or F8 Immunomodules) optimized for protein binding and containing 96 wells per plate. Each well was coated with taxol-BSA conjugate (prepared as in example 5) by adding 300 µL of taxol-BSA conjugate at 10 µg/mL in 0.05M sodium bicarbonate, pH=9.6, and incubating for three hours at room temperature. The wells were washed with 0.05M sodium bicarbonate, pH 9.6 and then were blocked with 400 µL of 5% sucrose, 0.2% sodium caseinate solution for 30 minutes at room temperature. After removal of the post-coat solution the plates were dried at 37° C. overnight.

Example 7b

Microtiter Plate Sensitization Procedure with Taxol Derivative 8

The ELISA method for measuring taxol concentrations was performed in polystyrene microtiter plates (Nunc Max-iSorp C8 or F8 Immunomodules) optimized for protein binding and containing 96 wells per plate. Each well was coated with taxol-BSA conjugate (prepared as in example 6) by adding 300 µL of taxol-BSA conjugate at 10 µg/mL in 0.05M sodium bicarbonate, pH=9.6, and incubating for three hours at room temperature. The wells were washed with 0.05M sodium bicarbonate, pH 9.6 and then were blocked with 400 µL of 5% sucrose, 0.2% sodium caseinate solution for 30 minutes at room temperature. After removal of the post-coat solution the plates were dried at 37° C. overnight.

Example 8a

Antibody Screening Procedure—Titer

The ELISA method for screening taxol antibodies (produced in example 4) was performed with the microtiter plates that were sensitized with taxol-BSA as described in example 7. The antibody screening assay was performed by diluting the antisera containing taxol antibodies (of example 4) to 1:100, 1:1,000, 1:10,000 and 1:100,000 in phosphate buffered saline containing 0.1% BSA and 0.01% thimerosal. For evaluation of monoclonal antibodies, hybridoma supernatants of example 4, which were found to be positive for the presence of antibody by the procedure of 8b, were diluted 1:2, 1:4, 1:8, 1:16, etc. in phosphate buffered saline containing 0.1% BSA and 0.01% thimerosal. To each well of taxol-BSA sensitized wells (prepared in example 7) 100 µL of diluted antibody was added and incubated for 10 minutes at room temperature with shaking. During this incubation antibody binds to the taxol-conjugate in the well. The wells of the plates were washed three times with 0.02 M TRIS, 0.9% NaCl, 0.5% Tween-80 and 0.001% Thimerosal, pH 7.8 to remove any unbound antibody. To detect the amount of taxol antibody bound to the taxol-BSA conjugate in the wells 100 µL of a goat anti-mouse antibody-HRP enzyme conjugate (Jackson Immunoresearch) diluted to a predetermined specific activity (approximately 1/2000) in PBS with 0.1% BSA, 0.05% ANS, 0.01% thimerosal, capable of binding specifically with murine immunoglobulins and producing a colored product when incubated with a substrate, were added to each well. After an incubation of 10 minutes at room temperature with shaking, during which the secondary-HRP conjugate binds to taxol antibodies in the wells, the plates were again washed three times to remove unbound secondary conjugate. To develop a measurable color in the wells, washing was followed by the addition of 100 µL of TMB (TMB Liquid Substrate, Sigma), a substrate for HRP, to develop color during a 10 minute incubation with shaking at room temperature. Following the incubation for color development, 50 µL of stop solution (1.5% sodium fluoride in di $H_2O$) was added to each well to stop the color development and after 10 seconds of shaking the absorbance was determined at 650 nm (Molecular Devices Plate Reader). The amount of antibody in a well was proportional to the absorbance measured and was expressed as the dilution (titer) resulting in an absorbance of 1.5. Titers were determined by graphing Log antibody dilution of the antibody measured (x-axis) vs. absorbance 650 nm (y-axis) and extrapolating the titer at an absorbance of 1.5. The titer determined the concentration (dilution) of antibody used in the indirect competitive Microtiter plate assay described in example 9.

Example 8b

Antibody Screening Procedure—Monoclonal Screening

The ELISA method for screening taxol monoclonal antibodies (produced in example 4) was performed with the microtiter plates that were sensitized with taxol-BSA as described in example 6. To each well of taxol-BSA sensitized wells (prepared in example 7b) 50 uL phosphate buffered saline containing 0.1% BSA and 0.01% thimerosal and then 50 µL of monoclonal culture supernatant were added and incubated for 10 minutes at room temperature with shaking. During this incubation antibody binds to the taxol-conjugate in the well. The wells of the plates were washed three times with 0.02 M TRIS, 0.9% NaCl, 0.5% Tween-80 and 0.001% Thimerosal, pH 7.8 to remove any unbound antibody. To detect the amount of taxol antibody bound to the taxol-BSA conjugate in the wells, 100 µL of a goat anti-mouse antibody-HRP enzyme conjugate (Jackson Immunoresearch) diluted to a predetermined specific activity (approximately $\frac{1}{2000}$) in PBS with 0.1% BSA, 0.05% ANS, 0.01% thimerosal, capable of binding specifically with murine immunoglobulins and producing a colored product when incubated with a substrate, were added to each well. After an incubation of 10 minutes at room temperature with shaking, during which the goat anti-mouse antibody-HRP enzyme conjugate binds to taxol antibodies in the wells, the plates were again washed three times to remove unbound goat anti-mouse antibody-HRP enzyme conjugate. To develop a measurable color in the wells, washing was followed by the addition of 100 µL of TMB (TMB Liquid Substrate, Sigma), a substrate for HRP, to develop color during a 10 minute incubation with shaking at room temperature. Following the incubation for color development, 50 µL of stop solution (1.5% sodium fluoride in di H2O) was added to each well to stop the color development and after 10 seconds of shaking the absorbance was determined at 650 nm (Molecular Devices Plate Reader). The amount of antibody in a well was proportional to the absorbance measured. Samples with an absorbance of greater than twice background were designated as positive.

Example 9a

Indirect Competitive Microtiter Plate Immunoassay Procedure Determining $IC_{50}$ and Cross-Reactivity The ELISA method for measuring taxol concentrations was performed with the microtiter plates that were sensitized with taxol-BSA described in example 7a. Taxol, baccatin III, 3'-p-hydroxypaclitaxel, 6-α-hydroxypaclitaxel and taxotere were diluted 10 fold in PBS or PBS containing 0.1% BSA and 0.01% thimerosal over a concentration range of 0.01 to 10,000 ng/mL. The assay was performed by incubating 50 µL of the analytes to be measured with 50 µL of antibody (produced in example 4) diluted to a titer determined in example 8a. During the 10 minute incubation (R.T., with shaking) there is a competition of antibody binding for the taxol conjugate in the well and the analyte in solution. Following this incubation the wells of the plate were washed three times with 0.02 M TRIS, 0.9% NaCl, 0.5% Tween-80 and 0.001% Thimerosal, pH 7.8 to remove any material that was not bound. To detect the amount of taxol antibody bound to the taxol-BSA conjugate in the wells, 100 µL of a secondary antibody which was a goat anti mouse antiglobulin antibody-HRP enzyme conjugate (Jackson Immunoresearch) diluted to a predetermined specific activity (approximately $\frac{1}{2000}$) in PBS with 0.1% BSA, 0.05% ANS, 0.01% thimerosal, capable of binding specifically with murine immunoglobulins and producing a colored product when incubated with a substrate, were added to each well. After an incubation of 10 minutes at room temperature with shaking, during which the secondary-HRP conjugate binds to taxol antibodies in the wells, the plates were again washed three times to remove unbound secondary conjugate. To develop a measurable color in the wells, washing was followed by the addition of 100 µL of TMB (TMB Liquid Substrate, Sigma), a substrate for HRP, to develop color in a 10 minute incubation with shaking at room temperature. Following the incubation for color development, 50 µL of stop solution (1.5% sodium fluoride in di H2O) was added to each well to stop the color development and after 10 seconds of shaking the absorbance was determined at 650 nm (Molecular Devices Plate Reader). The amount of antibody in a well was proportional to the absorbance measured and inversely proportional to the amount of taxol in the sample. The absorbance of the color in the wells containing analyte is compared to that with no analyte and a standard curve is generated. The $IC_{50}$ value for a given analyte was defined as the concentration of analyte that is required to inhibit 50% of the absorbance for the wells containing no analyte. The cross-reactivity of a given analyte was calculated as the ratio of the $IC_{50}$ for taxol to the $IC_{50}$ for baccatin III, 3'-p-hydroxypaclitaxel, 6-α-hydroxypaclitaxel and taxotere expressed as a percent. To evaluate the cross-reactivities of baccatin III, 3'-p-hydroxypaclitaxel, 6-α-hydroxypaclitaxel and taxotere with the taxol polyclonal antibodies generated in example 4, a pool of antisera was made from orbital bleeds. This pool combined the antibodies of four mice, which individually had $IC_{50}$ values of <20 ng/mL for taxol. When measured with this pool of antibodies the percent cross-reactivities relative to taxol for baccatin III, 3'-p-hydroxypaclitaxel, and 6-α-hydroxypaclitaxel was less than 10%. The cross-reactivity with 6-α-hydroxypaclitaxel was less than 60%. Results are in table I. To evaluate the cross-reactivities of baccatin III, 3'-p-hydroxypaclitaxel, 6-α-hydroxypaclitaxel and taxotere with the taxol monoclonal antibodies generated in example 4, hybridoma culture supernatants from selected subcloned monoclonals were used. When measured with two of these monoclonal antibodies the percent cross-reactivities relative to taxol for baccatin III, 3'-p-hydroxypaclitaxel, and 6-α-hydroxypaclitaxel was less than 6%. Results are in table II.

Example 9b

Indirect Competitive Microtiter Plate Immunoassay Procedure Determining $IC_{50}$ and Cross-Reactivity The ELISA method for measuring taxol concentrations was performed with the microtiter plates that were sensitized with taxol-BSA described in example 7b. Taxol, baccatin III, 3'-p-hydroxypaclitaxel, 6-α-hydroxypaclitaxel and taxotere were diluted 10 fold in PBS or PBS containing 0.1% BSA and 0.01% thimerosal over a concentration range of 0.01 to 10,000 ng/mL. The assay was performed by incubating 50 µL of the analytes to be measured with 50 µL of antibody (produced in example 4) diluted to a titer determined in example 8a. During the 10 minute incubation (R.T., with shaking) there is a competition of antibody binding for the taxol conjugate in the well and the analyte in solution. Following this incubation the wells of the plate were washed three times with 0.02 M TRIS, 0.9% NaCl, 0.5% Tween-80 and 0.001% Thimerosal, pH 7.8 to remove any material that was not bound. To detect the amount of taxol antibody bound to the taxol-BSA conjugate in the wells, 100 µL of a secondary antibody which was the goat anti mouse antiglobulin antibody-HRP enzyme conjugate (Jackson Immunoresearch) diluted to a predetermined specific activity (approximately $\frac{1}{2000}$) in PBS with 0.1% BSA, 0.05% ANS, 0.01% thimerosal, was added to each well. This secondary antibody was capable of binding specifically with murine immunoglobulins producing a colored product when incubated with a substrate. After an incubation of 10 minutes at room temperature with shaking, during which the secondary-HRP conjugate binds to taxol antibodies in the wells, the plates were again washed three times to remove unbound secondary conjugate. To develop a measurable color in the wells, washing was followed by the addition of 100 μL of TMB (TMB Liquid Substrate, Sigma), a substrate for HRP, to develop color in a 10 minute incubation with shaking at room temperature. Following the incubation for color development, 50 μL of stop solution (1.5% sodium fluoride in di $H_2O$) was added to each well to stop the color development and after 10 seconds of shaking the absorbance was determined at 650 nm (Molecular Devices Plate Reader). The amount of antibody in a well was proportional to the absorbance measured and inversely proportional to the amount of taxol in the sample. The absorbance of the color in the wells containing analyte is compared to that with no analyte and a standard curve is generated. The $IC_{50}$ value for a given analyte was defined as the concentration of analyte that is required to inhibit 50% of the absorbance for the wells containing no analyte. The cross-reactivity of a given analyte was calculated as the ratio of the $IC_{50}$ for taxol to the $IC_{50}$ for baccatin III, 3'-p-hydroxypaclitaxel, 6-α-hydroxypaclitaxel and taxotere expressed as a percent. To evaluate the cross-reactivities of baccatin III, 3'-p-hydroxypaclitaxel, 6-α-hydroxypaclitaxel and taxotere with the taxol antibodies generated in example 4, the pool of example 9a was used. When measured with this pool of antibodies, the percent cross-reactivities relative to taxol for baccatin III, 3'-p-hydroxypaclitaxel, 6-α-hydroxypaclitaxel and taxotere (docetaxel) were less than 2%. Results are in table I. When measured with selected monoclonal antibodies (as in example 9a) the percent cross-reactivities relative to taxol for baccatin III, 3'-p-hydroxypaclitaxel, and 6-α-hydroxypaclitaxel were less than 9%. Results are in table II.

TABLE I

Cross-reactivity of Competitive Immunoassay using polyclonal antibodies to taxol (example 4).

| | Microtiter Plate Sensitization | |
|---|---|---|
| Analyte | Taxol Derivative 8 | Taxol Derivative 5 |
| Taxol (Paclitaxel) | 100% | 100% |
| Docetaxel | 0.16% | ≦5% |
| 3'-p-Hydroxypaclitaxel | 0.57% | ≦10% |
| 6-α-Hydroxypaclitaxel | 1.60% | <58% |
| Baccatin III | 0.10% | 0.10% |

TABLE II

Cross-reactivity of Competitive Immunoassay using monoclonal antibodies to taxol (example 4).

| | Monoclonal Ab #1 Microtiter Plate Sensitization | | Monoclonal Ab #2 Microtiter Plate Sensitization | |
|---|---|---|---|---|
| Analyte | Taxol Derivative 8 | Taxol Derivative 5 | Taxol Derivative 8 | Taxol Derivative 5 |
| Taxol (Paclitaxel) | 100% | 100% | 100% | 100% |
| Docetaxel | 77% | 76% | 85% | 101% |
| 3'-p-Hydroxypaclitaxel | 8.1% | 5.9% | 1.5% | ≦2.3% |
| 6-α-Hydroxypaclitaxel | 6.5% | 5.1% | 2.9% | ≦4.6% |
| Baccatin III | 0.17% | 0.13% | 0.13% | ≦0.19% |

As seen from the above table the antibodies of this invention are not reactive with the major metabolites of taxol, but are reactive with taxol and taxol like drugs. While patients being administered taxol are not simultaneously administered docetaxel, these antibodies can be used in an immunoassay which can specifically detect and monitor taxol in the fluid samples of patients being treated with taxol.

What is claimed:

1. An immunoassay method for detecting taxol in a sample providing a mixture of a sample, containing an antibody selectively reactive with taxol and not substantially cross-reactive with both 6-α-hydroxypaclitaxel and 3'-p-hydroxypaclitaxel and a conjugate of a carrier or a polyamine polymer with a compound of the formula:

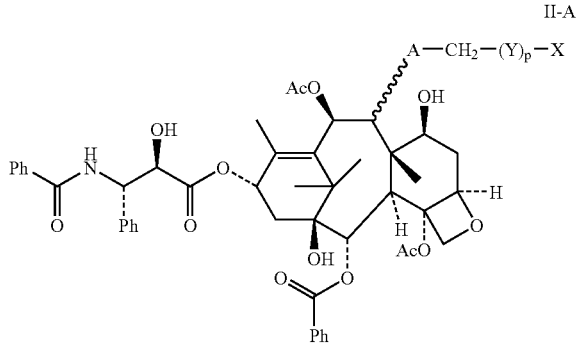

II-A wherein A is

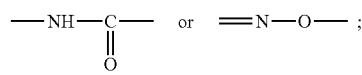

Y is an organic spacing group;
X is a terminal functional group capable of binding to said carrier or said polyamine polymer;
p is an integer from 0 to 1; and
Ph is phenyl
or compounds of the formula:

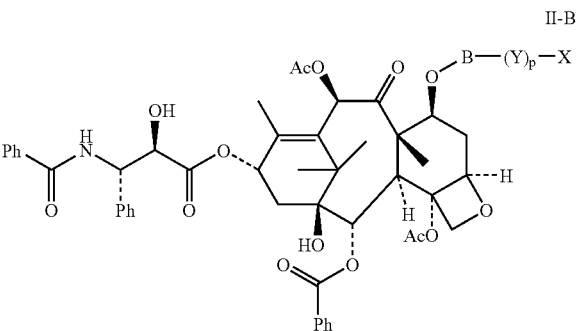

II-B wherein X, Y and p are as above and B is

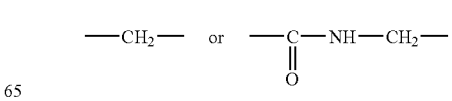

or mixtures thereof, causing the taxol in the sample and said conjugate to bind with said antibody and thereafter measuring the amount of said conjugate in said mixture which is bound or unbound to said antibody whereby the presence of taxol in the sample can be determined.

2. The immunoassay method of claim 1, wherein the sample is a human sample.

3. The immunoassay method of claim 2, wherein said antibody is generated from an immunogen comprising an immunogenic polymer linked to a compound of the formula:

II-A wherein p, X, Y and A are as in claim 1;
or a compound of the formula:

II-B wherein p, Y, X and B are as in claim 1;
and mixtures thereof.

4. The immunoassay method of claim 2, wherein the antibody is attached to a solid support.

5. The immunoassay method of claim 4, wherein the solid support is microtiter plates.

6. The immunoassay method of claim 4, wherein the solid support is nanoparticles.

7. An antibody which binds selectively to taxol and does not substantially bind to both 6-α-hydroxypaclitaxel and 3'-p-hydroxypaclitaxel.

8. The antibody of claim 7, wherein said antibody is derived from mice, rabbits or rats.

9. The antibody of claim 7, wherein said antibody is a monoclonal antibody.

10. The antibody of claim 7, wherein said antibody is derived from an immunogen of a polyamine polymer with a compound selected from the group consisting of compounds of the formula:

II-A wherein A is $$-NH-\overset{\overset{\displaystyle O}{\|}}{C}- \quad \text{or} \quad =N-O-\ ;$$

Y is an organic spacing group;
X is a terminal functional group capable of binding to a polyamine polymer;
p is an integer from 0 to 1; and
Ph is phenyl
or compounds of the formula:

II-B wherein X, Y and p are as above and B is $$-CH_2- \quad \text{or} \quad -\overset{\overset{\displaystyle O}{\|}}{C}-NH-CH_2-$$

or mixtures thereof.

11. The antibody of claim 10, wherein said antibody is derived from mice, rabbits or rats.

12. The antibody of claim 10, wherein said antibody is a monoclonal antibody.

13. The antibody of claim 11, wherein said antibody is a monoclonal antibody.

14. A kit for determining the presence of taxol in a patient sample comprising reagents in separate containers, the first of said containers containing as a reagents a conjugate of a carrier or a polyamine polymer with a compound selected from the groups consisting of compounds of the formula:

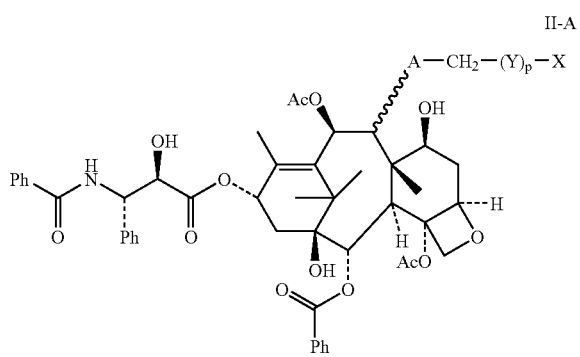

wherein A is

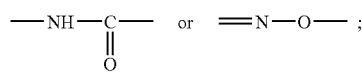

Y is an organic spacing group;
X is a terminal functional group capable of binding to said carrier or said a polyamine polymer
p is an integer from 0 to 1; and
Ph is phenyl
or a compound of the formula:

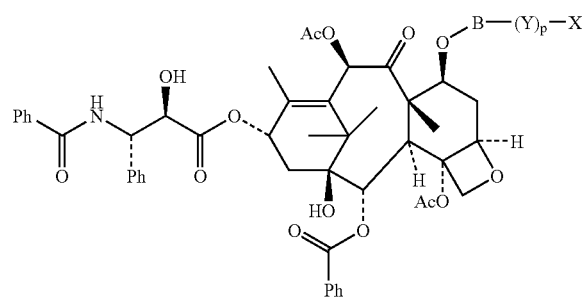

wherein X, Y and p are as above and B is

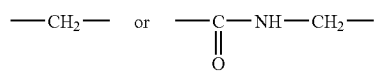

and mixtures thereof; and a second container containing an antibody substantially selectively reactive with taxol and not substantially cross-reactive to both 6-α-hydroxypaclitaxel and 3'-p-hydroxypaclitaxel.

15. The kit of claim 14, wherein said conjugate is present in a predetermined amount in said first container.

16. The kit of claim 15, wherein said kit is used to determine the amount of taxol in said sample.

17. The kit of claim 14, wherein, said antibody is generated from an immunogen of an immunogenic polyamine polypeptide linked to a compound selected from the group consisting of compounds of the formula:

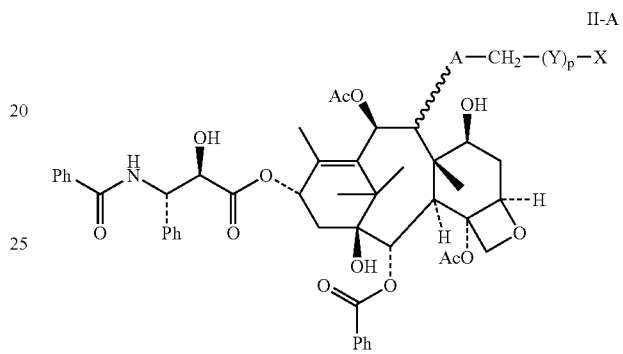

wherein A, Y, X and p are as in claim 11
compounds of the formula:

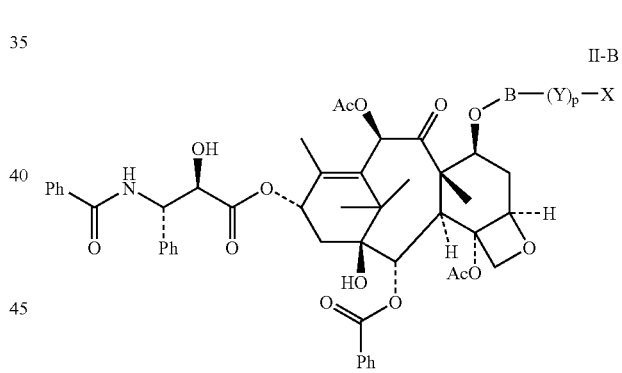

wherein p, Y, X and B are as in claim 11;
or mixtures thereof.

* * * * *